(12) United States Patent
Carpenter

(10) Patent No.: US 11,540,938 B2
(45) Date of Patent: Jan. 3, 2023

(54) MEDICAL HOT AIR BLOWER

(71) Applicant: Joseph Carpenter, Las Vegas, NV (US)

(72) Inventor: Joseph Carpenter, Las Vegas, NV (US)

( * ) Notice: Subject to any disclaimer, the term of this patent is extended or adjusted under 35 U.S.C. 154(b) by 887 days.

(21) Appl. No.: 16/427,937

(22) Filed: May 31, 2019

(65) Prior Publication Data
US 2020/0375792 A1    Dec. 3, 2020

(51) Int. Cl.
*A61F 7/00*    (2006.01)
*A61F 7/08*    (2006.01)
*A61F 7/02*    (2006.01)

(52) U.S. Cl.
CPC ........... *A61F 7/0085* (2013.01); *A61F 7/086* (2013.01); *A61F 2007/0048* (2013.01); *A61F 2007/0055* (2013.01); *A61F 2007/0087* (2013.01); *A61F 2007/0091* (2013.01); *A61F 2007/0222* (2013.01); *A61F 2007/083* (2013.01)

(58) Field of Classification Search
CPC ...... A61F 2007/0055; A61F 2007/0057; A61F 2007/0091; A61F 2007/083; A61F 7/0085; A61F 7/0086
See application file for complete search history.

(56) References Cited

U.S. PATENT DOCUMENTS

2017/0306984 A1* 10/2017 Peterson .............. F04D 29/665

\* cited by examiner

*Primary Examiner* — Kaitlyn E Smith
(74) *Attorney, Agent, or Firm* — The Thornton Firm, LLC

(57) ABSTRACT

A hot air producing system produces and stores hot air, and applies the stored hot air to a human body. The system includes a heating apparatus to heat the air, a temperature setting gauge to allow a user to set a desired temperature, a pressure gauge to measure a pressure of the air in the container, a pump to pump the hot air, a fill connection, an expandable container for receiving and storing the hot air, with a valve to connect to the fill connection such that the expandable container can receive the hot air, an adjustable flow release mechanism to allow a user to adjust an amount of flow of hot air out of the expandable container, and a flexible hose connected to the adjustable flow release mechanism, with a nozzle to direct the hot air to a portion of the human body.

15 Claims, 3 Drawing Sheets

MEDICAL HOT AIR BLOWER

FIELD OF THE INVENTION

The present invention pertains to an apparatus or system for generating and applying heated air to the human body to treat medical conditions. The heated air may be contained in a container and then applied as needed to the body.

BACKGROUND OF THE INVENTION

Urinary retention is a condition where a human can't pass urine even though the person may have a full bladder. This condition can have many causes, such as certain infections or medication, weakened bladder muscles, an injury to the pelvic or genital regions, any surgery requiring sedation or recent surgery in the genital, prostrate, rectal, pelvic or lower abdominal areas. There are also times when passing urine is required, however a person may not be able to void on command, such as for medical samples or after sexual intercourse to test for or avoid urinary tract infections. A know method of treatment of this condition is to apply heat to the genital area using water or a warm compress. However, applying heat using a heated air device is not common practice and while using such a device it is essential to produce heated air of the correct temperature which can be difficult. While certain conventional heated air devices could be used in non-conventional ways, these devices often produce unregulated heated air in excess of 140 degrees Fahrenheit, which could easily cause burns or discomfort to this very sensitive area of the human body.

Accordingly, a new apparatus is needed to apply heated air to this sensitive genital area of the human body.

SUMMARY OF THE INVENTION

Embodiments of the present invention provide a hot air producing system having a heat pump for pumping hot air, a temperature control for setting the temperature of the hot air, an expandable container for receiving and containing the hot air, and an adjustable release valve.

Embodiments of the invention include a hot air producing system for producing and storing hot air, and for applying the stored hot air to a human body. The hot air producing system may include a heating apparatus configured to heat the air to a temperature, the heating apparatus including a temperature setting gauge configured to allow a user to set a desired temperature to heat the air, a pressure gauge to measure a pressure of the air in the container, a pump to pump the hot air, and a fill connection; an expandable container for receiving the hot air from the heating apparatus and storing the hot air therein, the expandable container including a valve to connect to the fill connection of the heating apparatus such that the expandable container can receive the hot air from the heating apparatus; an adjustable flow release mechanism connected to an outlet of the expandable container, the adjustable flow release mechanism being configured to allow a user to adjust an amount of flow of hot air out of the expandable container; and a flexible hose connected to the adjustable flow release mechanism, the flexible hose having a nozzle configured to direct the hot air out of the flexible hose, wherein the flexible hose allows a user to direct the hot air to a portion of the human body.

The hot air producing system may further include an insulated case for receiving the expandable container therein, the insulated case comprising a material having insulative properties to retain heat in the hot air in the expandable container.

Further objects, features, and advantages of the present invention over the prior art will become apparent from the detailed description which follows, when considered with the figures provided herein.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

Embodiments of the invention provide a hot air producing apparatus configured to pump the hot air into a container under pressure. The container can then be used to temporarily store the hot air and to apply the hot air to the human body or for other purposes.

Figure 1:
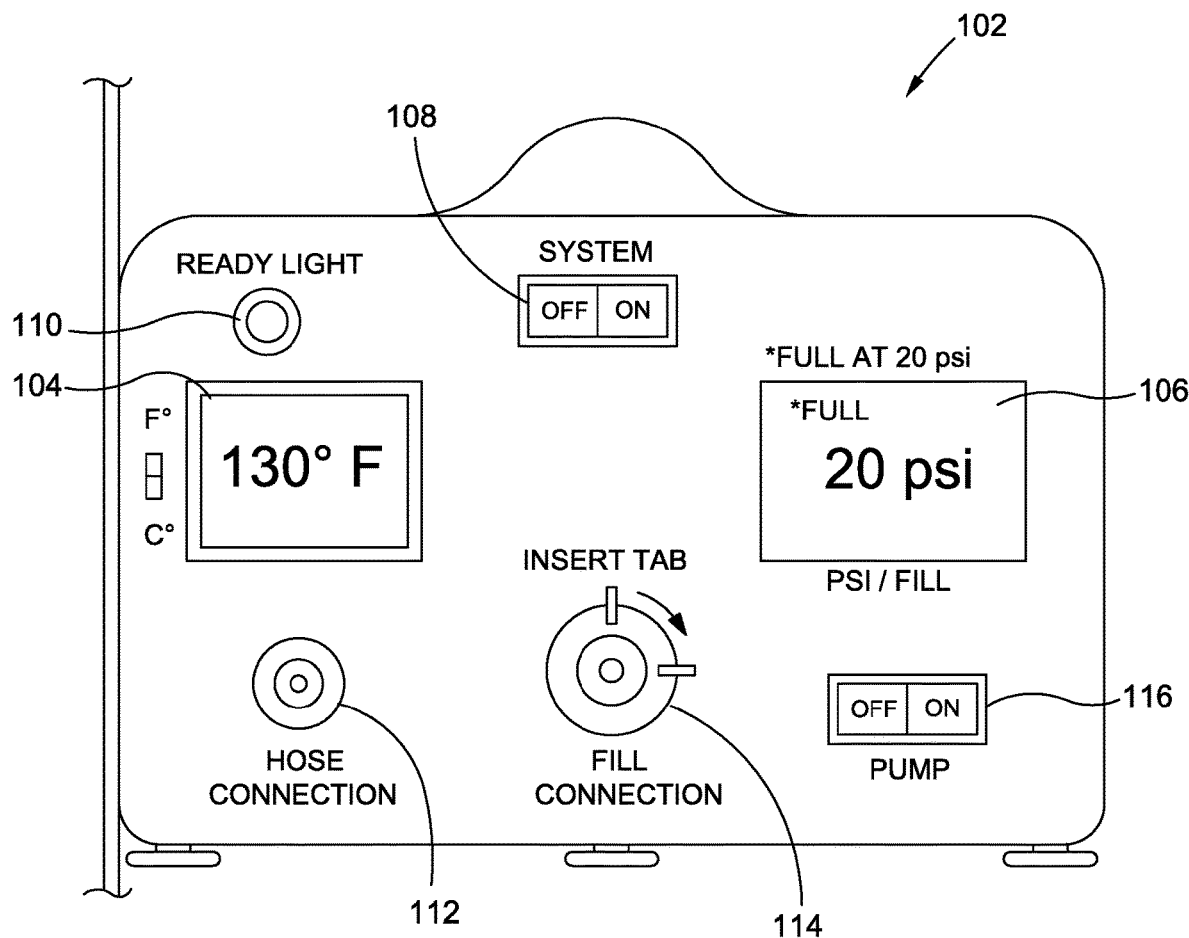
FIG. 1 is a front perspective view of a hot air producing apparatus in accordance with embodiments of the invention.

A front view of the hot air producing apparatus 102 is illustrated in FIG. 1 in accordance with preferred embodiments of the invention. The hot air producing apparatus 102 includes an air temperature gauge 104 (which can be switched between Celsius and Farenheiht), a pressure setting gauge 106, a system power on/off switch 108, a ready light 110, a hose connection 112, a fill connection 114, and a pump on/off switch 116.

The hot air producing apparatus 102 may include a heater device (not shown) such as a conventional heat pump to heat air and to pump the heated air under pressure. The heated air may be pumped either through the hose connection 112 or the fill connection 114 to fill a container with the hot air.

The temperature of the hot air can be set using the temperature gauge 104, which can be set to read either Celsius or Fahrenheit. A control (not shown) can be used to adjust the temperature to a desired level, such as with a numeric keypad or touchscreen, or even from a remote source connected to the hot air producing apparatus 102.

The pressure gauge 106 can be used to monitor pressure in psi, for example. The hot air producing apparatus 102 can be configured to pump hot air into a container to fill the container to a desired pressure. The hot air producing apparatus 102 can be configured to automatically shut off the pumping of the hot air when the container reaches the desired or a preset pressure.

The system power on/off switch 108 can be used to turn on or off all power to the system. The power may be supplied through a convention power cord, or be supplied by one or more batteries within the hot air producing apparatus 102. The hot air producing apparatus 102 may be configured to have containers receive hot air at any desired temperature and until full. In preferred embodiments, the hot air producing apparatus 102 may fill containers until a full pressure is reached, and the full pressure may be 20 psi as shown in FIG. 1, although other pressures could be used. The hot air producing apparatus 102 may be configured to automatically stop pumping hot air when the full pressure is reached.

The ready light 110 can be used to indicate when the hot air producing apparatus 102 is ready to begin pumping air at the desired temperature. The hot air producing apparatus 102 may need time to warm up a heating element to produce hot air of the desired temperature, and the ready light can thus be used to indicate when the apparatus is sufficiently warmed up to begin pumping the heated air.

The hose connection 112 may include a connector adapted to fit a hose with a corresponding connector of a particular type. The type of connectors used can be varied.

The fill connection 114 may be adapted to connect directly to a connector of a container, where a hose is not used. The fill connection 114 may have a connector of a different type than the hose connection 112.

The pump on/off switch 116 is used to turn the pump on (or off) to begin (or stop) pumping hot air through either the hose connection 112 or the fill connection 114. The switch may be configured to not function until the ready light is lit indicating the air can be pumped at the desired temperature.

The hot air producing apparatus 102 may include a processor and a memory (not shown in the figures), with the memory containing software configured to be run by the processor to control the hot air producing apparatus 102 to perform any of the functionality described herein.

Figure 2:
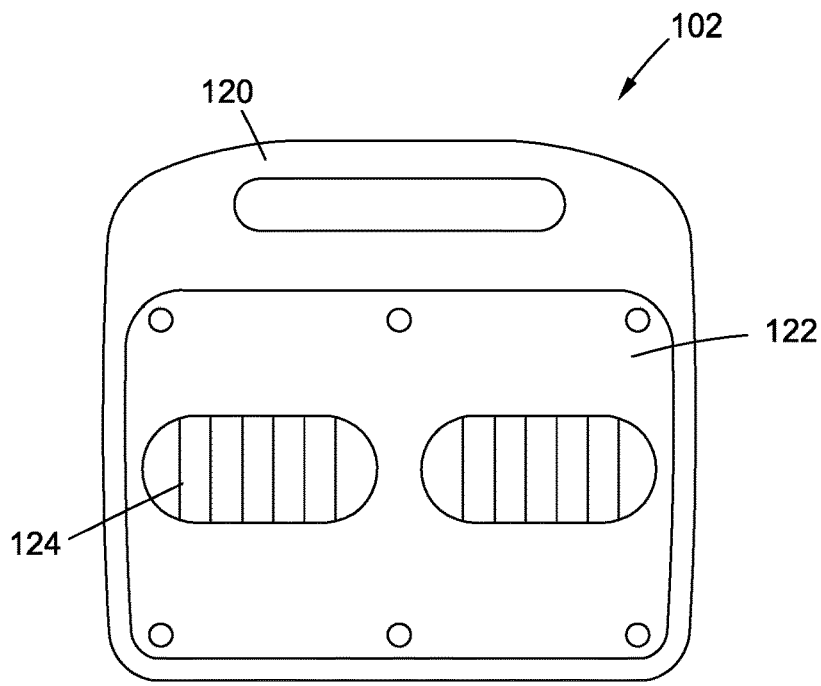
FIG. 2 is a side perspective view of the hot air producing apparatus in accordance with embodiments of the invention.

FIG. 2 illustrates a side view of the hot air producing apparatus 102. The side of the hot air producing apparatus 102 includes a handle 120 for carrying the hot air producing apparatus 102, and air vents 124 to cool the hot air producing apparatus 102. The air vents may be on an access panel 122.

Figure 3:
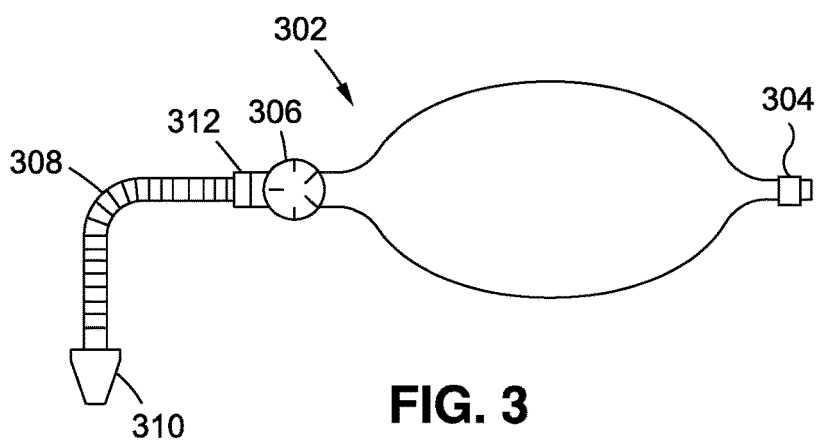
FIG. 3 is a perspective view of expandable container for containing hot air in accordance with embodiments of the invention.

FIG. 3 illustrates a container 302 for containing hot air produced by the hot air producing apparatus. The container 302 is configured to function with the hot air producing apparatus, and may be included as a part thereof. The container 302 may include a fill valve 304, an adjustable flow release valve 306, a flexible plastic tube 308, and air nozzle 310 and a connector 312. The container 302 is expandable, and may be an elastic fill bag, for example. The container may be formed from an elastic material such as natural rubber, synthetic rubber, nitrile rubber, silicone rubber, urethane rubber, chloroprene rubber, polyether rubber, chloroprene rubber, Ethylene Vinyl Acetate.

The fill valve 304 may be configured to connect to the fill connection 114 on the front of the hot air producing apparatus 102. When the pump of the hot air producing apparatus 102 is turned on with the fill valve 304 connected to the fill connection 114, hot air is pumped into the container 302 where the hot air can be stored and later used for application to the human body.

The flow release valve 306 is configured to allow a user to adjust a flow amount of hot air being release by, for example, turning of the valve 306. The flow release valve may include an off position, at which no air is released, and it may allow progressively more air to be release as the valve 306 is turned away from the off position.

The connector 312 is adapted to connect the air holding portion of the container 302 to the flexible hose 308. The flow release valve may be positioned on either side of the connector 312, although in a preferred embodiment, the flow release valve is positioned between the connector 312 and the flexible tube 308.

The flexible tube 308 allows the air nozzle 310 to be positioned by a user as desired to direct the hot air to a desired location. The flexible tube 308 may be made from various flexible materials, such as rubber, plastic, polyurethane, PVC, Nomex, Hypalon, thermoplastic, etc.

Figure 4:
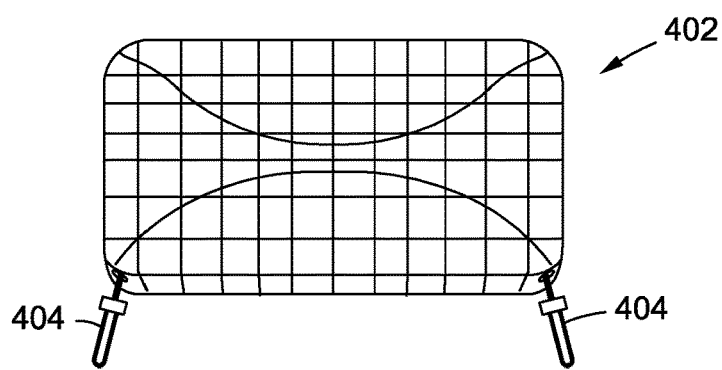
FIG. 4 is a perspective view of expandable insulated case for retaining the expandable container in accordance with embodiments of the invention.

FIG. 4 illustrates an insulated case 402 for holding the container 302. The case 402 is insulated to help the air in the container 302 to retain its heated condition over the course of time after the air is put in the container and before it is used. The insulated case may also be formed from a material that is stretchable, so that the case 402 can expand as air is put in the container 302. For example, the insulated case may be made from materials such as a quilted material, Thinsulate, or other thermal fabric product to provide insulation, or a stretchable thermo fabric to provide insulation and be stretchable. The case 402 may include one or more tightening cords 404 to tighten the case 402 around the container 302. The case 402 may be sized to somewhat tightly fit the container 302 therein, while being able to stretch to a larger size as needed. The case 402 may include one or more zippers (not shown) or other ways of closing the insulated case 402 around the container 302.

Figure 5:
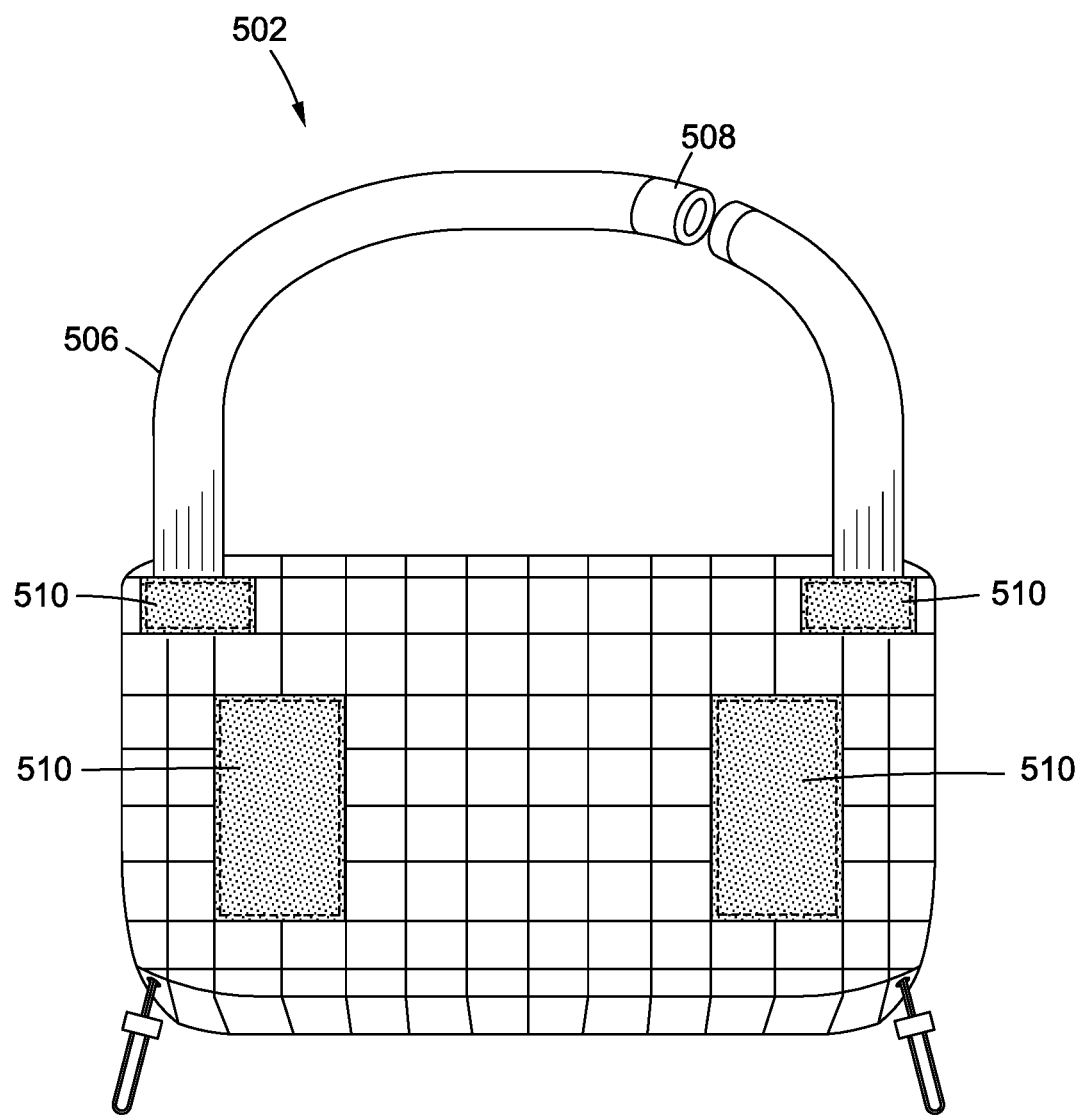
FIG. 5 is a view of an alternative expandable insulated case for retaining the expandable container in accordance with embodiments of the invention.

FIG. 5 illustrates another insulated case 502 having additional features. The insulated case 502 has a strap or handle 506. The strap 506 may have an adjustable length. The strap 506 may include connectors 508 allowing the strap to be disconnected into two pieces and reconnected. This allows the strap to be connected around objects to retain the insulated case in place. For example, the strap 506 be connected to a hook on a wall or table, to a bed post or rail, to a rail on a bathtub or toilet, around a human wrist, etc.

The insulated case 502 may also include attachment points 510. The attachment points 510 could be Velcro strips or other means of attachment. The attachment points 510 may be placed at various points on the insulated case 502. Any number of attachment points 510 may be used. Corresponding attachments points may be placed on an object, such as a wall, a bed, a toilet, etc., to which the insulated case 502 is to be attached. For example, if the attachments points 510 are Velcro strips, corresponding Velcro strips can be placed on an object to which the insulated case 502 is to be attached.

It will be understood that the above described arrangements of apparatus and the method there from are merely illustrative of applications of the principles of this invention and many other embodiments and modifications may be made without departing from the spirit and scope of the invention as defined in the claims.

What is claimed is:

1. A hot air producing system for producing and storing hot air, and for applying the stored hot air to a human body, comprising:

a heating apparatus configured to heat air to a temperature, the heating apparatus including a temperature setting gauge configured to allow a user to set a desired temperature to heat the air, a pressure gauge to measure a pressure of the air, a pump to pump the hot air, and a fill connection;

an expandable container for receiving the hot air from the heating apparatus and storing the hot air therein, the expandable container including a valve to connect to the fill connection of the heating apparatus such that the expandable container can receive the hot air from the heating apparatus;

an adjustable flow release mechanism connected to an outlet of the expandable container, the adjustable flow release mechanism being configured to allow a user to adjust an amount of flow of hot air out of the expandable container; and a flexible hose connected to the adjustable flow release mechanism, the flexible hose having a nozzle configured to direct the hot air out of the flexible hose, wherein the flexible hose allows a user to direct the hot air to a portion of the human body.

2. The hot air producing system of claim 1, further comprising an insulated case for receiving the expandable container therein, the insulated case comprising a material having insulative properties to retain heat in the hot air in the expandable container.

3. The hot air producing system of claim 2, wherein the insulated case comprises a material having insulative and expandable properties.

4. The hot air producing system of claim 2, wherein the insulated case comprises a material selected from a quilted material, Thinsulate, or other thermal fabric material.

5. The hot air producing system of claim 2, wherein the expandable container comprises a material having elastic properties.

6. The hot air producing system of claim 5, wherein the expandable container comprises a material selected from natural rubber, synthetic rubber, nitrile rubber, silicone rubber, urethane rubber, chloroprene rubber, polyether rubber, chloroprene rubber, Ethylene Vinyl Acetate.

7. The hot air producing system of claim 1, wherein the pump is configured to automatically stop pumping the hot air when the pressure gauge reaches a full pressure.

8. The hot air producing system of claim 2, further comprising attachment points on the insulated case for attaching the hot air producing system to an object.

9. A hot air producing and storing apparatus for producing and storing hot air, and for applying the stored hot air to a human body, comprising:

a heating apparatus configured to heat air to a temperature, the heating apparatus including a temperature setting gauge configured to allow a user to set a desired temperature to heat the air, a pressure gauge to measure a pressure of the air, a pump to pump the hot air, and a fill connection;

an expandable container for receiving the hot air from the heating apparatus and storing the hot air therein, the expandable container including a valve to connect to the fill connection of the heating apparatus such that the expandable container can receive the hot air from the heating apparatus;

an insulated case for receiving the expandable container therein, the insulated case comprising a material having insulative properties to retain heat in the hot air stored in the expandable container; and a flexible hose connected to an outlet of the expandable container, the flexible hose having a nozzle configured to direct the hot air out of the flexible hose, wherein the flexible hose allows a user to direct the hot air to a portion of the human body.

10. The hot air producing and storing apparatus of claim 9, wherein the insulated case comprises a material having insulative and elastic properties.

11. The hot air producing and storing apparatus of claim 9, wherein the insulated case comprises a material selected from a quilted material, Thinsulate, or other thermal fabric material.

12. The hot air producing and storing apparatus of claim 9, wherein the expandable container comprises a material having elastic properties.

13. The hot air producing and storing apparatus of claim 12, wherein the expandable container comprises a material selected from natural rubber, synthetic rubber, nitrile rubber, silicone rubber, urethane rubber, chloroprene rubber, polyether rubber, chloroprene rubber, Ethylene Vinyl Acetate.

14. The hot air producing and storing apparatus of claim 9, wherein the pump is configured to automatically stop pumping the hot air when the pressure gauge reaches a full pressure.

15. The hot air producing and storing apparatus of claim 9, further comprising attachment points on the insulated case for attaching the hot air producing and storing apparatus to an object.

* * * * *